United States Patent [19]
Hoard et al.

[11] Patent Number: 5,994,547
[45] Date of Patent: Nov. 30, 1999

[54] PROCESS FOR PREPARING BENZO[B] THIOPHENES

[75] Inventors: David Warren Hoard, Greenwood; Wayne Douglas Luke, West Lafayette, both of Ind.

[73] Assignee: Eli Lilly and Company, Indianapolis, Ind.

[21] Appl. No.: 09/069,500

[22] Filed: Apr. 29, 1998

Related U.S. Application Data

[60] Provisional application No. 60/045,156, Apr. 30, 1997.

[51] Int. Cl.$^6$ .................................................. C07D 409/12
[52] U.S. Cl. ........................... 546/202; 540/536; 548/525
[58] Field of Search ........................... 540/536; 546/202; 548/525

[56] References Cited

U.S. PATENT DOCUMENTS

| | | | |
|---|---|---|---|
| 3,394,125 | 7/1968 | Crenshaw | 514/320 |
| 3,413,305 | 11/1968 | Crenshaw | 546/202 |
| 4,133,814 | 1/1979 | Jones et al. | 546/202 |
| 4,358,593 | 11/1982 | Jones et al. | 546/202 |
| 4,380,635 | 4/1983 | Peters | 546/202 |
| 4,418,068 | 11/1983 | Jones et al. | 514/324 |
| 5,223,510 | 6/1993 | Gubin et al. | 514/299 |
| 5,395,842 | 3/1995 | Labrie et al. | 514/320 |
| 5,455,315 | 10/1995 | Paine et al. | 526/79 |
| 5,470,854 | 11/1995 | Angerer et al. | 514/233 |
| 5,472,962 | 12/1995 | Sagamihara et al. | 514/233.5 |
| 5,482,949 | 1/1996 | Black et al. | 514/324 |
| 5,552,412 | 9/1996 | Cameron et al. | 514/317 |
| 5,629,425 | 5/1997 | Labell et al. | 546/202 |

FOREIGN PATENT DOCUMENTS

| | | |
|---|---|---|
| 0062503 | 10/1982 | European Pat. Off. . |
| 0062504 | 10/1982 | European Pat. Off. . |
| 605 193 | 7/1994 | European Pat. Off. . |
| 2097392 | 4/1982 | United Kingdom . |
| 2096608 | 10/1982 | United Kingdom . |
| 2097788 | 11/1982 | United Kingdom . |
| WO93/10741 | 6/1993 | WIPO . |
| WO95/10513 | 4/1995 | WIPO . |

OTHER PUBLICATIONS

Kirk–Othmer "Encyclopedia of chemical technology" J. Wiley & Sons, p. 946–964, 1983.
Jones, C.D., et al, *J. Med. Chem.* 27(8)1057–1066 (1971).
Romeo Wagner, *Synthetic Organic Chemistry*, (171–172) (1953).
Jones, C.D., et al *J. Med Chem.* 35(5) 931–938(1992).
Kym, R.P. et al, *J. Med. Chem.,* 36 (24), 3911–3921 (1993).
Jackson, T.G., et al *J. Chem. Soc.* 1728–1729 (1969).
Kametani, et al *J. Org. Chem.* 41 (15) 2545–2547 (1976).
Crenshaw, R.R., et al *J. Med. Chem.* 14(12) 1185–1190 (1971).

*Primary Examiner*—Ceila Chang
*Attorney, Agent, or Firm*—Gilbert T. Voy

[57] ABSTRACT

The preparation of benzo[b]thiophenes by the acylation of alkoxy protected starting materials followed by demethylation using essentially odorless thiol compounds are provided herewith. Demethylation may be carried out in the same reaction vessel without isolation of the acylated, protected material.

13 Claims, No Drawings

PROCESS FOR PREPARING BENZO[B] THIOPHENES

CROSS REFERENCE TO RELATED APPLICATIONS

This application claims priority to provisional application Ser. No. 60/045,156, filed Apr. 30, 1997.

FIELD OF THE INVENTION

This invention pertains to the field of pharmaceutical chemistry and provides an advantageous process for preparing benzo[b]thiophenes. More specifically, the process relates to the preparation of 6-hydroxy-2-(4-hydroxyphenyl)-3-benzo[b]thiophenes by dealkylating 6-alkoxy-2-(4-alkoxyphenyl)-3-benzo[b]thiophenes using a thiol compound.

BACKGROUND OF THE INVENTION

U.S. Pat. No. 4,133,814 teaches a variety of compounds that may be prepared by the process of this invention. That patent describes the use of phenacyl, halophenacyl, and alkyl protecting groups. The processes descibed therein do not, however, suggest the particularly advantageous way to use the methyl protecting group which is provided by this invention.

Chem. Lett. 97-98 (1979), Tet. Let. 5211–14 (1978), and J. Org. Chem. 45: 4275–77 (1980) disclosed the use of aluminum halide thiols as reagents for the demethylation of various aliphatic and aromatic ethers.

U.S. Pat. No. 4,380,635 teaches the preparation of 6-hydroxy-2-(4-hydroxyphenyl)-3-[4-(2-aminoethoxy) benzoyl]benzo[b]thiophenes. The patent describes the acylation of a benzothiophene in the presence of aluminum chloride or bromide with an acid chloride or bromide followed by the addition of a sulfur compound to cleave the methoxy ether linkages, which finally affords 6-hydroxy-2-(4-hydroxyphenyl)-3-[4-(2-aminoethoxy)benzoyl]benzo[b] thiophenes upon hydrolytic work-up. Specific sulfur compounds disclosed as useful for cleaving the methoxy protecting groups include methanethiol, ethanethiol, isopropanethiol, butanethiol, diethyl sulfide, dibutyl sulfide, ethyl propyl sulfide, butyl isopropyl sulfide, dimethyl sulfide, methyl ethyl sulfide, methyl phenyl sulfide, ethyl phenyl sulfide, butyl phenyl sulfide, benzenethiol, and methionine. Ethanethiol is identified as the preferred agent, and all but two of the examples provided herein utilize this particular thiol. The other thiols employed are dimethyl sulfide and methionine. Methyl ether cleavage was not complete with methionine. Instead, the reaction mixture consisted primarily of a mixture of the two possible monomethyl ether products.

U.S. Pat. No. 4,948,829 discloses 2-methyl-5-t-butyl benzenethiol as a stabilizer of vinyl chloride polymers. Many of the benzothiophene compounds prepared by the process of the instant invention are described in U.S. Pat. No. 4,133, 814.

A major disadvantage of previous processes described in the art is the odor associated with the sulfur compounds employed, and with the sulfur containing by-products which are generated in the process. The threshold of human detection for ethanethiol is 0.47 ppb. The odor is a primary deterrent to large scale manufacture of many commercially significant benzothiophenes using processes known in the art.

Thus, it would be a significant contribution to the art to provide processes for the preparation of benzothiophenes which employ essentially odorless sulfur compounds.

SUMMARY OF THE INVENTION

The present invention provides a method for removing alkyl groups from alkoxy-protected benzothiophenes, and specifically from 6-methoxy-2-(4-methoxyphenyl)-3-[4-(2-aminoethoxy)benzoyl]benzo[b]thiophenes utilizing an essentially odorless thiol, 2-methyl-5-t-butyl benzenethiol, to generate product mixtures that are also essentially odorless.

Thus, the instant invention provides methods for producing various hydroxybenzothiophenes that do not require elaborate ventilation equipment, incineration, or chemical scrubbing to eliminate odors associated with other thiols which may be employed.

The invention provides a process for preparing a compound of formula VI:

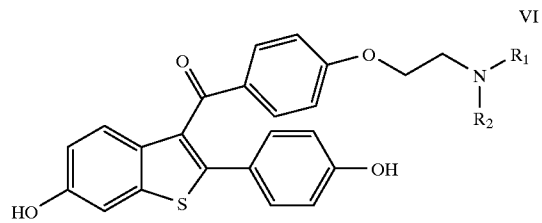

wherein $R_1$ and $R_2$ are independently $C_1$–$C_4$ alkyl, or combine to form, together with the nitrogen to which they are attached, piperidinyl, pyrrolidinyl, methylpyrrolidinyl, dimethylpyrrolidinyl, or hexamethyleneimino, or a pharmaceutically acceptable salt or solvate thereof; which comprises:

acylating a compound of formula II:

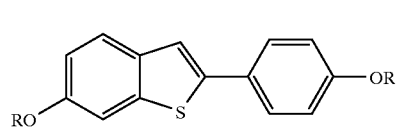

wherein R is independently $C_1$–$C_6$ alkyl; with an acylating agent of formula III:

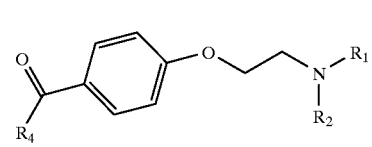

wherein $R_4$ is chloro or bromo, in the presence of a Lewis acid catalyst, and adding 2-methyl-5-t-butyl benzenethiol to the reaction mixture, or isolating the acylated benzothiophene and subsequently treating it with 2-methyl-5-t-butyl benzenethiol in the presence of a Lewis acid catalyst.

The invention further provides a process for dealkylating compounds of formula IV:

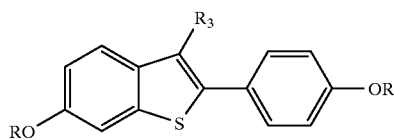

IV wherein R₃ represents hydrogen or an acyl group of the formula:

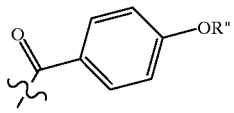

wherein R" represents $C_1$–$C_4$ alkyl or —$(CH_2)_n NR_1R_2$, wherein n is 1 to 4, and $R_1$ and $R_2$ are independently $C_1$–$C_4$ alkyl, or combine to form, together with the nitrogen to which they are attached, piperidinyl, pyrrolidinyl, methylpyrrolidinyl, dimethylpyrrolidinyl, or hexamethyleneimino, or a pharmaceutically acceptable salt or solvate thereof, which includes reacting a compound of formula IV with 2-methyl-5-t-butyl benzenethiol in the presence of a Lewis acid catalyst.

DETAILED DESCRIPTION OF THE INVENTION

In this document, all temperatures are stated in degrees Celsius. All amounts, ratios, concentrations, proportions and the like are stated in weight units unless otherwise stated, except for ratios of solvents which are in volume units.

In the formulas above, the general terms bear their usual meanings. For example, the term $C_1$–$C_4$ primary or secondary alkyl refers to groups such as methyl, ethyl, propyl, sec-butyl, isobutyl, and the like. The term $C_1$–$C_4$ alkyl includes the above groups and also includes t-butyl. The term $C_1$–$C_4$ alkoxy refers to straight or branched chain lower alkoxy groups such as methoxy, ethoxy, propoxy, isopropoxy, butyloxy, and the like. The term $C_1$–$C_6$ alkyl includes $C_1$–$C_4$ alkyl, and also refers to straight or branched chain pentyl or hexyl. The term unbranched $C_1$–$C_4$ alkyl refers to methyl, ethyl, propyl, and butyl.

The term "Lewis acid catalyst" refers to the type of catalyst described in Olah, "Friedel-Crafts and Related Reactions," Interscience Publishing Co., New York, 1963 and includes metal halides such as aluminum bromide, aluminum chloride, boron trifluoride, boron trichloride, boron tribromide, titanium tetrachloride, titanium tetrabromide, stannic chloride, stannic bromide, bismuth trichloride, ferric chloride and the like. A preferred Lewis acid of this invention is an aluminum halide chosen from the list of aluminum chloride, aluminum bromide, or aluminum iodide. A particularly preferred aluminum halide is aluminum chloride.

As mentioned above, the invention includes the pharmaceutically acceptable salts of the compounds defined by formula VI. Although generally neutral, a compound of this invention can possess a sufficiently basic functional group, and accordingly react with any of a number of inorganic and organic acids to form a pharmaceutically acceptable salt. See, for example, Berge, S. M, Bighley, L. D., and Monkhouse, D. C., *J. Pharm. Sci.*, 66, 1, 1977.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

It should be recognized that the particular counterion forming a part of any salt of this invention is not of a critical nature, so long as the salt as a whole is pharmacologically acceptable and as long as the counterion does not contribute undesired qualities to the salt as a whole.

This invention provides a convenient process which acylates an alkyl protected, and preferably methyl-protected, starting compound, and then dealkylates, preferably demethylates, it to obtain the desired dihydroxy product. The acylation and demethylation are preferably performed in successive steps in a single reaction mixture. The following group of representative products of the process and of this invention will be mentioned, to assure that the reader fully understands the overall purpose of the process:

6-hydroxy-2-(4-hydroxyphenyl)-3-[4-(2-dimethylaminoethoxy)-benzoyl]benzo[b]thiophene;

3-[4-(2-ethoxymethylaminoethoxy)benzoyl]-6-hydroxy-2-(4-hydroxylphenyl)benzo[b]thiophene;

3-[4-(2-ethoxyisopropylaminoethoxy)benzoyl]-6-hydroxy-2-(4-hydroxyphenyl)benzo[b]thiophene;

3-[4-(2-dibutylaminoethoxy)benzoyl]-5-hydroxy-2-(4 hydroxyphenyl)benzotb]thiophene;

3-[4-(2-(1-methylpropyl)methylaminoethoxy]-benzoyl]-6-hydroxy-2-(4-hydroxyphenyl)benzo[b]thiophene;

6-hydroxy-2-(4-hydroxyphenyl)-3-[4-[2-di(2-methyl propyl)aminoethoxy]benzoyl]benzo[b]thiophene;

6-hydroxy-2-(4-hydroxyphenyl)-3-[4-(2-pyrrolidino ethoxy)benzoyl]benzo[b]thiophene;

6-hydroxy-2-(4-hydroxyphenyl)-3-[4-(2-piperidino-ethoxy)benzoyl]benzo[b]thiophene;

6-hydroxy-2-(4-hydroxyphenyl)-3-t4-(2-morpholinoethoxy)-benzoyl]benzo[b]thiophene; and 3-[4-(2-hexamethyleneiminoethoxy)benzoyl]-6-hydroxy-2-(4-hydroxyphenyl)benzo[b]thiophene.

The final 6-hydroxy-2-(4-hydroxyphenyl)-3-[4-(2-aminoethoxy)benzoyl]benzo[b]thiophene compounds are tissue specific estrogen agonist/antagonists and, thus, are useful for estrogenic, antiestrogenic, and antiandrogenic therapy. Accordingly, they are useful in treating pathological conditions of endocrine target organs, which conditions are dependent or partially dependent on an estrogen or on an androgen. Such conditions include mammary cancer, mammary fibrocystic disease, cancer of the prostate, and benign prostatic hypertrophy.

U.S. Pat. No. 4,131,814 teaches that certain of the compounds are also useful as anticancer and antifertility drugs. The antiestrogenic and antiandrogenic efficacy of a preferred compound prepared by this invention, 6-hydroxy-2-(4-hydroxyphenyl)-3-[4-(2-piperidinoethoxy)benzoyl]benzo[b]thiophene, is explained in further detail in U.S. Pat. No. 4,413,068.

The dose of these compounds to be administered to a human is rather widely variable. It should be noted that it may be necessary to adjust the dose of a compound when it is administered in the form of a salt, such as a laurate, the salt-forming moiety of which has an appreciable molecular weight. The general range of effective administration rates of the compounds is from about 0.05 mg/kg/day to about 50 mg/kg/day. A preferred rate range is from about 0.1 mg/kg/day to about 10 mg/kg/day, and the most highly preferred range is from about 0.1 mg/kg/day to about 5 mg/kg/day. It is often practical to administer the daily dose of a compound in portions at various hours of the day.

The route of administration of the compounds is not critical. The compounds are known to be absorbed from the alimentary tract, and so it is usually preferred to administer a compound orally for reasons of convenience. However, the compounds may equally effectively be administered percutaneously, or as suppositories for absorption by the rectum, if desired in a given instance.

The compounds are usually administered as pharmaceutical compositions. All of the usual types of compositions may be used including tablets, chewable tablets, capsules, solutions, parenteral solutions, troches, suppositories, and suspensions. Compositions are formulated to contain a daily dose, or a convenient fraction of a daily dose, in a dosage unit, which may be a single tablet or capsule or a convenient volume of a liquid. In general, compositions contain from about 0.000006% to about 60% of compound, depending on the desired dose, and the type of composition to be used.

The activity of the compounds does not depend on the composition in which it is administered or on the concentration of the composition. Thus, the compositions are chosen and formulated solely for convenience and economy.

The preferred benzothiophene products of this process are those wherein $R_1$ and $R_2$ combine to form, together with the nitrogen to which they are attached, piperidinyl and pyrrolidinyl.

The process of the instant invention leading to the 6-hydroxy-2-(4-hydroxyphenyl)-3-(4-hydroxybenzoyl)benzo[b]thiophene final products is shown in Scheme I.

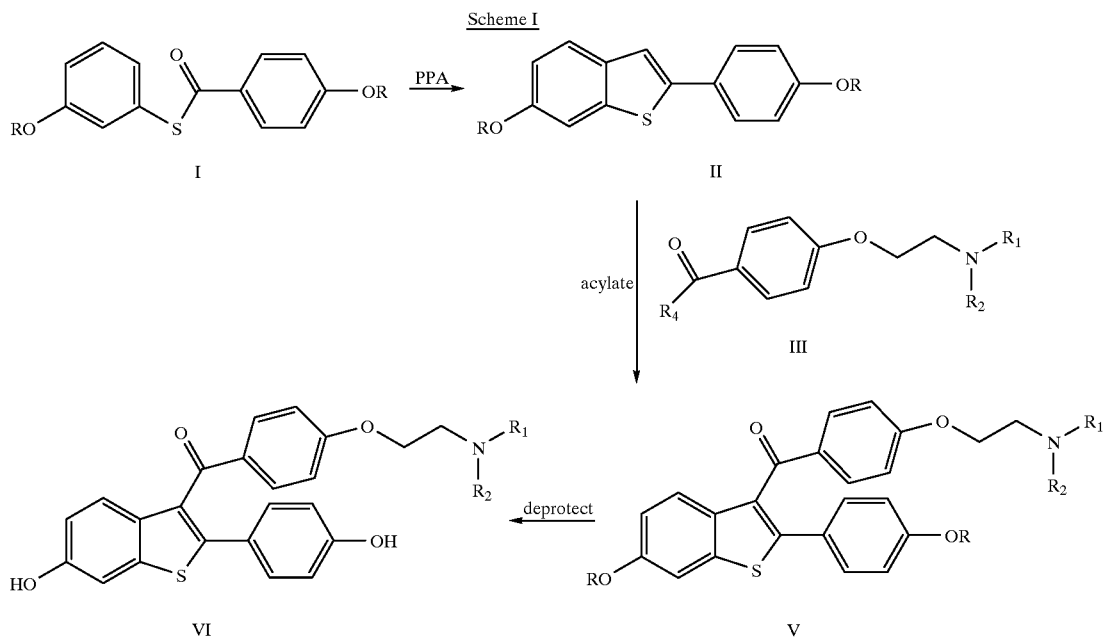

wherein R, $R_1$, $R_2$, and $R_4$ are as defined above.

The methyl-protected starting material (II) is most easily obtained by a synthesis which is exemplified below in Example 1. The process is carried out by reacting 3-methoxy benzenethiol and α-bromomethoxy acetophenone in the presence of a strong base at a relatively low temperature, to form α-(3-methoxyphenylthio)-4-methoxyacetophenone (I), which is then cyclized with an agent such as polyphosphoric acid at a high temperature to obtain the desired starting compound (II).

The acylation of this invention is a Friedel-Crafts acylation and is carried out in the usual way, using aluminum chloride or bromide, preferably the chloride, as the acylation catalyst. The acylation is ordinarily carried out in an inert solvent, typically an organic solvent which is not significantly attacked under the conditions is used. For example, halogenated solvents such as dichloromethane, 1,2-dichloroethane, chloroform, and the like, may be used, as well as aromatics, such as benzene and chlorobenzene. It is preferred to use a halogenated solvent, particularly chlorobenzene.

It has been found that toluene is rather easily acylated under the conditions used in the Friedel-Crafts acylation step, and so it is important, when toluene is used in an earlier step of the process, to remove it as completely as possible from the protected starting compound (II), to avoid reaction of toluene with the acylating agent (III).

The acylations may be carried out at temperatures from about −30° C. to about 100° C., preferably at about ambient temperature, in the range of about 15° C. to about 30° C.

The acylating agent is an active form of the appropriate benzoic acid. A preferred acylating agent is a compound of formula III and is shown in Scheme I. The preferred acylating agents are those wherein $R_4$ is chlorine. Thus, the most highly preferred acylating agents are 4-(2-piperidinoethoxy)benzoyl chloride, 4-(2-[3-methylpyrrolidino]ethoxy)benzoyl chloride and 4-(2-pyrrolidinoethoxy)benzoyl chloride.

The examples below demonstrate that the acyl chloride used as an acylating agent may be prepared from the corresponding carboxylic acid by reaction with a typical chlorinating agent, such as thionyl chloride. Care must be taken to remove any excess chlorinating agent from the acyl chloride, however. Most conveniently, the acyl chloride is formed in situ, and the excess chlorinating agent is distilled off under vacuum.

Equimolar amounts of the benzothiophene (II) and the acylating agent (III) may be used effectively. If desired, a small excess of either reactant may be added to assure that the other is fully consumed.

It is preferred to use a large excess of the acylation catalyst, such as about 2–12 moles per mole of product, and preferably about 5–10 moles.

The acylation is a rapid reation. Economically brief reaction times such as from about 15 minutes to a few hours provide high yields of the acylated intermediate. Longer reaction times may be used if desired but are not usually advantageous. As usual, the use of lower reaction temperatures calls for relatively longer times.

Subsequent to the acylation step, the acylated benzothiophene (V) may be isolated and purified prior to dealkylation, or, preferably, may be immediately dealkylated. Preferably, the acylated dimethoxybenzothiophene is demethylated by adding the 2-methyl-5-t-butyl benzenethiol to the reaction mixture.

It has been found that demethylation is most efficient when a substantial molar excess of the 2-methyl-5-t-butyl benzenethiol is used, in the range of from about 4 to about 10 moles per mole of the starting benzothiophene (V). The process can be carried out, although less efficiently, with a smaller amount of the 2-methyl-5-t-butyl benzenethiol in the range of about 2 or 3 moles per mole of starting compound. It is also possible to use a small amount of the 2-methyl-5-t-butyl benzenethiol, such as 2 or 3 moles per mole of starting compound, and to improve the yield by the addition of about 1 to 3 moles of an alkali metal halide, such as sodium, potassium, or lithium chloride, iodide or bromide. (A similar effect of sodium iodide is shown by Niva et al. *Tet. Lett.* 22: 4239-40 (1981).

The dealkylation of the dialkoxy compounds by the 2-methyl-5-t-butyl benzenethiol is typically conducted along with a Lewis acid. More specifically, an aluminum halide, preferably, aluminum chloride is employed. Where the acylation is followed immediately by dealkylation, no additional Lewis acid is required. Where the dialkoxy compound is isolated prior to dealkylation, a Lewis acid will, of course, be added to the dealkylation reaction mixture. The amount of Lewis acid ranges from about 1 to 10, and preferably about 6, equivalents of the Lewis acid based on the number of moles of dialkoxy compound (V).

The demethylation reaction goes well at about ambient temperature, in the range of from about −30° C. to about 30° C. However, the demethylation step is preferably carried out at temperatures in the range of from about 30° C. to about 100° C. Reaction times in the range of from about 1 to 24 hours have been found to be adequate.

After the product has been demethylated, it is recovered and isolated by conventional means. It is customary to add water to decompose the complex of the acylation catalyst. Addition of dilute aqueous acid, for this purpose, is advantageous. The product precipitates in many instances, or may be extracted with an organic solvent according to conventional methods. The examples below further illustrate the isolation.

The product of this process (VI) may be recovered as the free amine, or as an acid addition salt as is conventional in the synthesis of amine-containing products. For example, the compounds may be isolated as a salt of inorganic or organic acids such hydrobromic acid, hydroiodic acid, sulfonic acids including such agents as naphthalenesulfonic, methanesulfonic, and toluenesulfonicacids, sulfuric acid, nitric acid, phosphoric acid, tartaric acid, pyrosulfuric acid, metaphosphoric acid, succinic acid, formic acidphthalic acid, lactic acid, and the like, preferably hydrochloric acid, citric acid, benzoic acid, maleic acid, acetic acid, or propionic acid. For example, the product may be isolated as the hydrochloride simply by using dilute hydrochloric acid to decompose the catalyst complex.

The following examples further illustrate the manner in which this invention is carried out.

EXAMPLES

All reactions were run under an atmosphere of nitrogen. Products were identified and quantified by reverse phase high pressure liquid chromatography using a Zorbax RX C8 (25 cm×0.46 cm, 5~m) column and a detection wavelength of 280 nm. The mobile phase was 0.075 M phosphate at pH 22.0 [3.40 g of potassium phosphate monobasic into 1.0 L of water, pH adjusted to 2.0 with 3.5 ml of 85% phosphoric acid] and acetonitrile. The following gradient was employed at a flow rate of 1.0 ml/min:

| Time | % acetonitrile |
| --- | --- |
| 0 | 30 |
| 12 | 30 |
| 14 | 75 |
| 16 | 30 |
| 25 | 30 |

Preparation 1

6-Methoxy-2-(4-Methoxyphenyl)benzo[b]thiophene

A 100 g portion of 3-methoxy benzenethiol and 39.1 g of potassium hydroxide dissolved in 300 ml of water were added to 750 ml of denatured ethanol, and the flask was put in a cooling bath. A total of 164 g of α-bromo-1-methoxyacetophenone was then added in small portions, and the mixture was stirred for 10 minutes in the cooling bath after the addition was complete and then for 3 hours at ambient temperature. The solvent was then evaporated off in vacuo, and 200 ml. of water was added. The mixture was extracted with ethyl acetate, and the organic layer was washed twice with water, twice with aqueous sodium bicarbonate solution and twice with aqueous sodium chloride solution. The organic layer was then dried over magnesium sulfate, filtered and evaporated in vacuo to obtain 202 g of crude α-(3-methoxyphenylthio)-4-methoxyacetophenone, which was recrystallized with hexane to obtain 158 g of preferred product, m.p. 53° C.

A 124 g portion of the above intermediate was added in small portions to 930 g of polyphosphoric acid at 85° C. The temperature rose to 95° C. during the addition, and the mixture was stirred at 90° C. for 30 minutes after the addition was complete, and was then stirred an additional 45 minutes while it cooled without external heating. One liter of crushed ice was then added to the mixture, and the external ice bath was applied to control the temperature while the ice melted and diluted the acid. Five hundred ml of additional water was added, and the light pink precipitate was filtered off and washed, first with water and then with methanol. The solids were dried in vacuo at 40° C. to obtain 119 g of crude 6-methoxy-2-(4-methoxyphenyl)benzo[b]thiophene. The crude product was slurried in hot methanol, filtered, and washed with cold methanol, and the solids were recrystallized from 4 liters of ethyl acetate, filtered, washed with hexane, and dried to obtain 68 g of the desired intermediate product, m.p. 187° C.–190.5° C.

Preparation 2

6-Methoxy-2-(4-Methoxyphenyl)-3-[4-(2-Piperidinoethoxy)benzoyl]benzo[b]thiophene Hydrochloride A 3 g portion of 4-(2-piperidinoethoxy)-benzoic acid hydrochloride, was combined with 20 ml of 1,2-dichloroethane and 2 drops of dimethylformamide at −20° C., and 4 ml of phosgene was added. The mixture was stirred for 90 minutes while the temperature was slowly raised to reflux, and then for 30 minutes at reflux. An additional 80 ml of 1,2-dichloroethane was added, and then 2.7 g of 6-methoxy-2-(4-methoxypheny)benzo[b]thiophene. An 8.68 g portion of aluminum chloride was added, and the mixture was stirred for 3 hours. An additional 2.66 g of aluminum chloride was added, and the mixture was stirred for 16 more hours. The mixture was poured into a large amount of 1/1 dichloromethane/dilute aqueous hydrochloric acid. Additional dichloromethane containing little methanol was added until distinct layers separated. The water layer was extracted several times with dichloromethane containing a little methanol, and the organic layers were combined and washed with water and with aqueous sodium chloride. The organic layer was then filtered and evaporated to an oil, which was dissolved in dichloromethane and a little methanol, and extracted with about 20 ml of 5% aqueous sodium hydroxide, and then with water, aqueous ammonium chloride, and water. The organic layer was then evaporated to about 5 g of oil, which was dissolved in acetone. Diethyl ether was added, and impurities precipitated and were filtered out. The filtrate was evaporated to about 3.4 g of foam, which was purified by preparative high-pressure liquid phase chromatography on silica gel, eluting with 1.5% methanol in chloroform. The product-containing fractions were combined and evaporated to obtain the desired product as 1.88 g of yellow oil; m/e 501.19% by electron impact high resolution mass spectrometry; absorption maximum at 16.50 on the infrared spectrum in chloroform; $l_{max}(e)$: 296 (32, 500) on the ultraviolet spectrum in ethanol.

Example 1

6-Hydroxy-2-(4-Hydroxyphenyl)-3-[4-(2-Piperidinoethoxy)benzoyl]benzo[b]thiophene Hydrochloride To a suspension of 1.00 g of 6-methoxy-2-(4-methoxyphenyl)-3-[4-(2-piperidinoethoxy) benzoyl]benzo[b]thiophene hydrochloride in 10 ml of chlorobenzene at 10° C. was added 1.49 g of aluminum chloride, followed by 0.74 g if 2-methyl-5-tert-butylthiophenol. After the dark red oily mixture was heated at 35° C. for 5.75 hours, the mixture was cooled to 10° C. and 6 ml of tetrahydrofuran was added, followed by 2 ml of 20% hydrochloric acid, and then 6 ml of water, maintaining a temperature of 10–20° C. After the mixture was stirred for 30 minutes, the cream-colored solid was collected by filtration and washed with 8 ml of water. The solid was dried under vacuum at 43° C. to give 1.00 g of crude product, which was identified by HPLC as 6-hydroxy-2-(4-hydroxyphenyl)-3-[4-(2-piperidinoethoxy) benzoyl]-benzo[b]thiophene hydrochloride.

Example 2

6-Hydroxy-2-(4-Hydroxyphenyl)-3-[4-(2-Piperidinoethoxy) benzoyl]benzo[b]thiophene Hydrochloride Using the same quantities of reagents and the same work-up protocol as given in Example 3, the reaction was repeated at 60° C. and allowed to stir at this temperature for 4.25 hours before the product was isolated. The cream-colored solid was dried in vacuo at 43° C. to give 0.82 g of crude product, which was identified by HPLC as 6-hydroxy-2-(4-hydroxyphenyl)-3-[4-(2-piperidinoethoxy)-benzoyl] benzo[b]thiophene hydrochloride.

Example 3

6-Hydroxy-2-(4-Hydroxyphenyl)-3-[4-(2-Piperidinoethoxy)benzoyl]benzo[b]thiophene Hydrochloride To a mixture of 30.0 g of 4-(2-piperidinoethoxy)benzoic acid, hydrochloride and 2.0 ml of dimethylformamide in 500 ml of dichloromethane was added 10.5 ml of oxalyl chloride at ambient temperature. After stirring overnight, 1.2 ml additional oxalyl chloride was added and the mixture allowed to stir 30 minutes before the volatiles were evaporated to give a light green solid. The solid was re-slurried in 100 ml dichloromethane and the volatiles once again evaporated. After repeating this process once more, the material was combined with 27.0 g of 6-methoxy-2-(4-methoxyphenyl) benzo[b]thiophene and 500 ml chlorobenzene, and the mixture cooled to 5° C. 80.0 g of aluminum chloride was added to the mixture, and after it was warmed to 28° C., the dark red mixture was allowed to stir for 3 hours. After cooling the mixture to 20° C., 39.7 g of 2-methyl-5-tert-butylthiophenol was added, and the mixture was warmed to 35° C. and stirred for 21 hours. The dark red oily mixture was then cooled to 20° C., and 300 ml of tetrahydrofuran was added, followed by 100 ml of 20% hydrochloric acid, and 300 ml of water. After the mixture was stirred for 30 minutes, the tan solid was collected by filtration and washed with 1×50 ml of water, followed by 2×75 ml water. The solid was dried in a vacuum oven at 60° C. to give 60.6 g of crude product, which was identified by HPLC and assigned a potency of 54.1% as 6-hydroxy-2-(4-hydroxyphenyl)-3-[4-(2-piperidinoethoxy) benzoyl]benzo[b]thiophene hydrochloride.

We claim:

1. A process for preparing a compound of formula VI

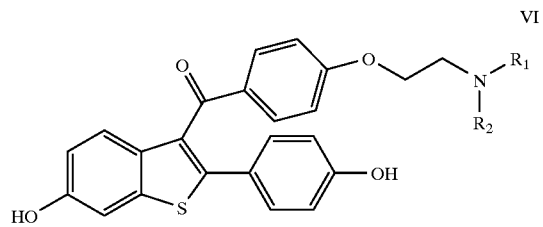

wherein $R_1$ and $R_2$ are independently $C_1$–$C_4$ alkyl, or combine to form, together with the nitrogen to which they are attached, piperidinyl, pyrrolidinyl, methylpyrrolidinyl, dimethylpyrrolidinyl, or hexamethyleneimino, or a pharmaceutically acceptable salt or solvate thereof; which comprises:

reacting a compound of formula V

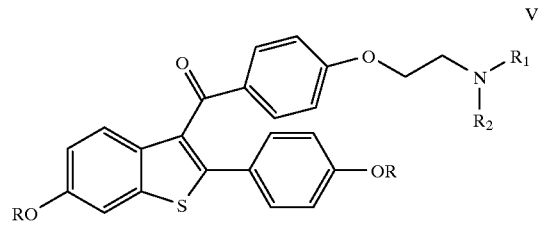

wherein R is independently $C_1$–$C_6$ alkyl, and $R_1$ and $R_2$ are as defined above;
with 2-methyl-5-t-butyl benzenethiol in the presence of a Lewis acid.

2. A process according to claim 1, wherein said compound of formula V is reacted with said 2-methyl-5-t-butyl benzenethiol in a solvent which is a halobenzene, and wherein said Lewis acid is an aluminum halide.

3. A process according to claim 2, wherein said halobenzene is chlorobenzene, and wherein said aluminum halide is aluminum chloride.

4. A process according to claim 2, wherein said compound of formula V is treated with said 2-methyl-5-t-butyl benzenethiol in the presence of an excess of aluminum halide.

5. A process according to claim 4, wherein R is methyl.

6. A process according to claim 5, wherein said compound of formula V and said 2-methyl-5-t-butyl benzenethiol are present at a molar ratio of about 1:1.

7. A process according to claim 5, wherein said molar ratio of said 2-methyl-5-t-butyl benzenethiol to said compound of formula V is from about 2:1 to about 12:1.

8. A process according to claim 5, wherein the temperature is from about −30° C. to about 100° C.

9. A process for preparing a compound of formula VI

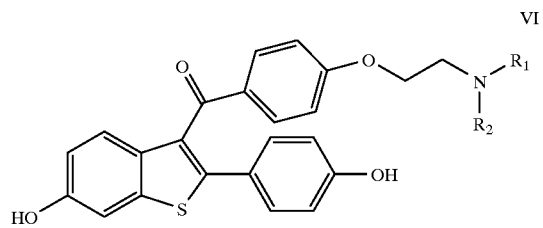

wherein $R_1$ and $R_2$ are independently $C_1$–$C_4$ alkyl, or combine to form, together with the nitrogen to which they are attached, piperidinyl, pyrrolidinyl, methylpyrrolidinyl, dimethylpyrrolidinyl, or hexamethyleneimino, or a pharmaceutically acceptable salt or solvate thereof; which comprises:

acylating a compound of formula II

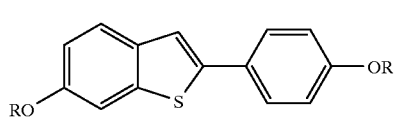

wherein R is independently $C_1$–$C_6$ alkyl;
with a compound of formula III

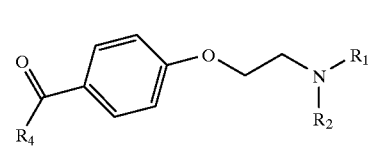

wherein $R_4$ is chloro or bromo, and $R_1$ and $R_2$ are as defined above,
in the presence of a Lewis acid, and adding 2-methyl-5-t-butyl benzenethiol to the reaction mixture.

10. A process according to claim 9 wherein R is methyl.

11. A process for preparing a compound of formula VIII:

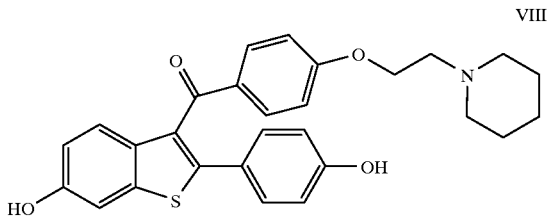

or a pharmaceutically acceptable salt or solvate thereof; which comprises:

(a) reacting a compound of formula VII

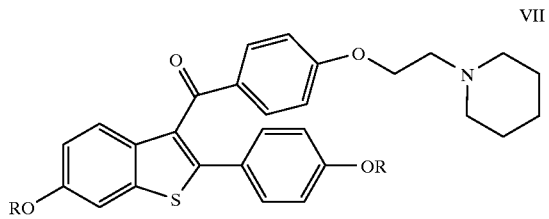

wherein R is independently $C_1$–$C_6$ alkyl, with 2-methyl-5-t-butyl benzenethiol in chlorobenzene in the presence of aluminum chloride;

(b) acidifying the mixture of step (a); and (c) optionally isolating said compound of formula VIII.

12. A process according to claim 11, wherein the molar ratio of said 2-methyl-5-t-butyl benzenethiol to said compound of formula VII is from about 2:1 to about 12:1.

13. A process according to claim 11, wherein R is methyl.

* * * * *